United States Patent
Aliamiri

(10) Patent No.: US 10,939,835 B2
(45) Date of Patent: Mar. 9, 2021

(54) METHOD AND APPARATUS FOR OBTAINING HIGH QUALITY PHOTOPLETHYSMOGRAM DATA FROM WEARABLE

(71) Applicant: Samsung Electronics Co., Ltd., Suwon-si (KR)

(72) Inventor: Alireza Aliamiri, San Jose, CA (US)

(73) Assignee: Samsung Electronics Co., Ltd., Suwon-si (KR)

( * ) Notice: Subject to any disclaimer, the term of this patent is extended or adjusted under 35 U.S.C. 154(b) by 302 days.

(21) Appl. No.: 15/851,281

(22) Filed: Dec. 21, 2017

(65) Prior Publication Data
US 2019/0142288 A1 May 16, 2019

Related U.S. Application Data

(60) Provisional application No. 62/586,107, filed on Nov. 14, 2017.

(51) Int. Cl.
*A61B 5/1455* (2006.01)
*A61B 5/024* (2006.01)
*A61B 5/00* (2006.01)
*A61B 5/0245* (2006.01)

(52) U.S. Cl.
CPC ........ *A61B 5/02427* (2013.01); *A61B 5/0245* (2013.01); *A61B 5/02438* (2013.01); *A61B 5/6885* (2013.01); *A61B 5/7264* (2013.01); *A61B 2560/0462* (2013.01); *A61B 2562/0261* (2013.01)

(58) Field of Classification Search
None
See application file for complete search history.

(56) References Cited

U.S. PATENT DOCUMENTS

| | | | | |
|---|---|---|---|---|
| 2011/0245633 | A1* | 10/2011 | Goldberg | A61B 5/165 600/301 |
| 2013/0324865 | A1 | 12/2013 | Yavelov et al. | |
| 2015/0164349 | A1* | 6/2015 | Gopalakrishnan | A61B 5/02055 600/508 |
| 2016/0360986 | A1* | 12/2016 | Lange | A61B 5/6829 |
| 2018/0338721 | A1* | 11/2018 | Wang | A61B 5/6814 |

FOREIGN PATENT DOCUMENTS

| | | |
|---|---|---|
| JP | 2008-521533 A | 6/2008 |
| JP | 4786968 B2 | 10/2011 |
| JP | 5061848 B2 | 10/2012 |
| JP | 6010982 B2 | 10/2016 |
| KR | 10-0236200 B1 | 12/1999 |
| KR | 10-1784484 B1 | 10/2017 |

\* cited by examiner

*Primary Examiner* — Marjan Fardanesh
(74) *Attorney, Agent, or Firm* — Lewis Roca Rothgerber Christie LLP

(57) ABSTRACT

A wearable device includes: a wristband; at least one PPG sensor mounted on the wristband and configured to output a measured PPG signal corresponding to vital signals of a wearer of the wristband; a neural network based controller configured to receive the measured PPG signal from the at least one PPG sensor and to generate commands in real time based on a quality of the PPG signal to adjust at least one selected from a position, a tension, and an orientation of the wristband to achieve a desired PPG signal quality.

18 Claims, 6 Drawing Sheets

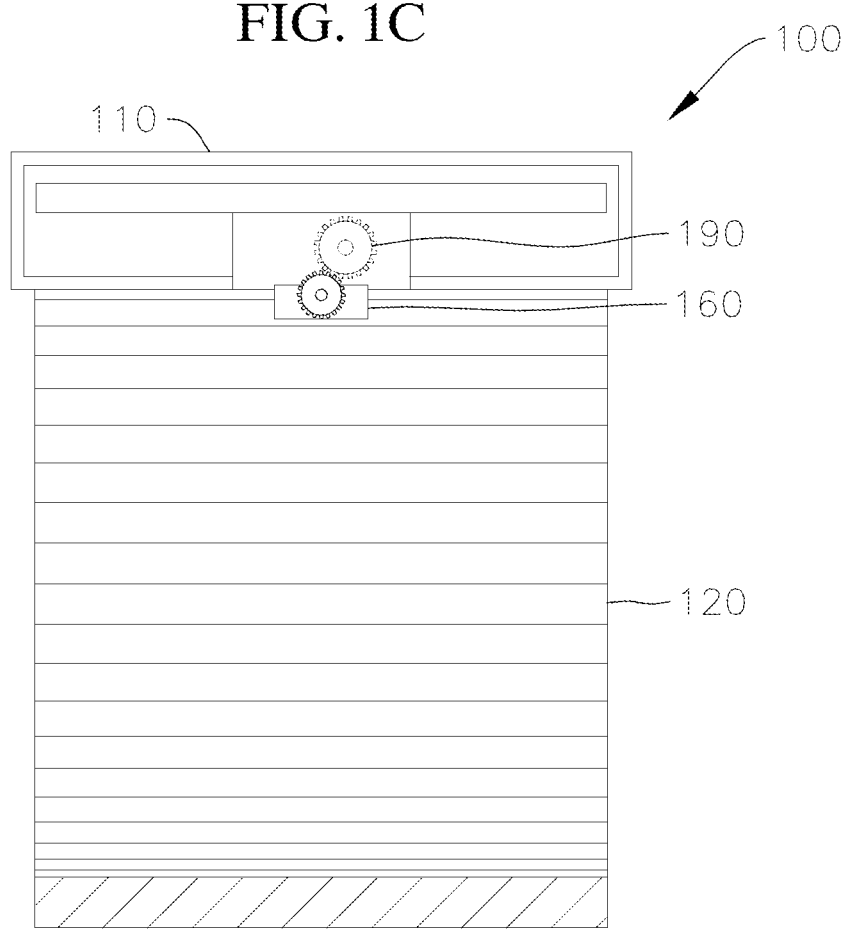

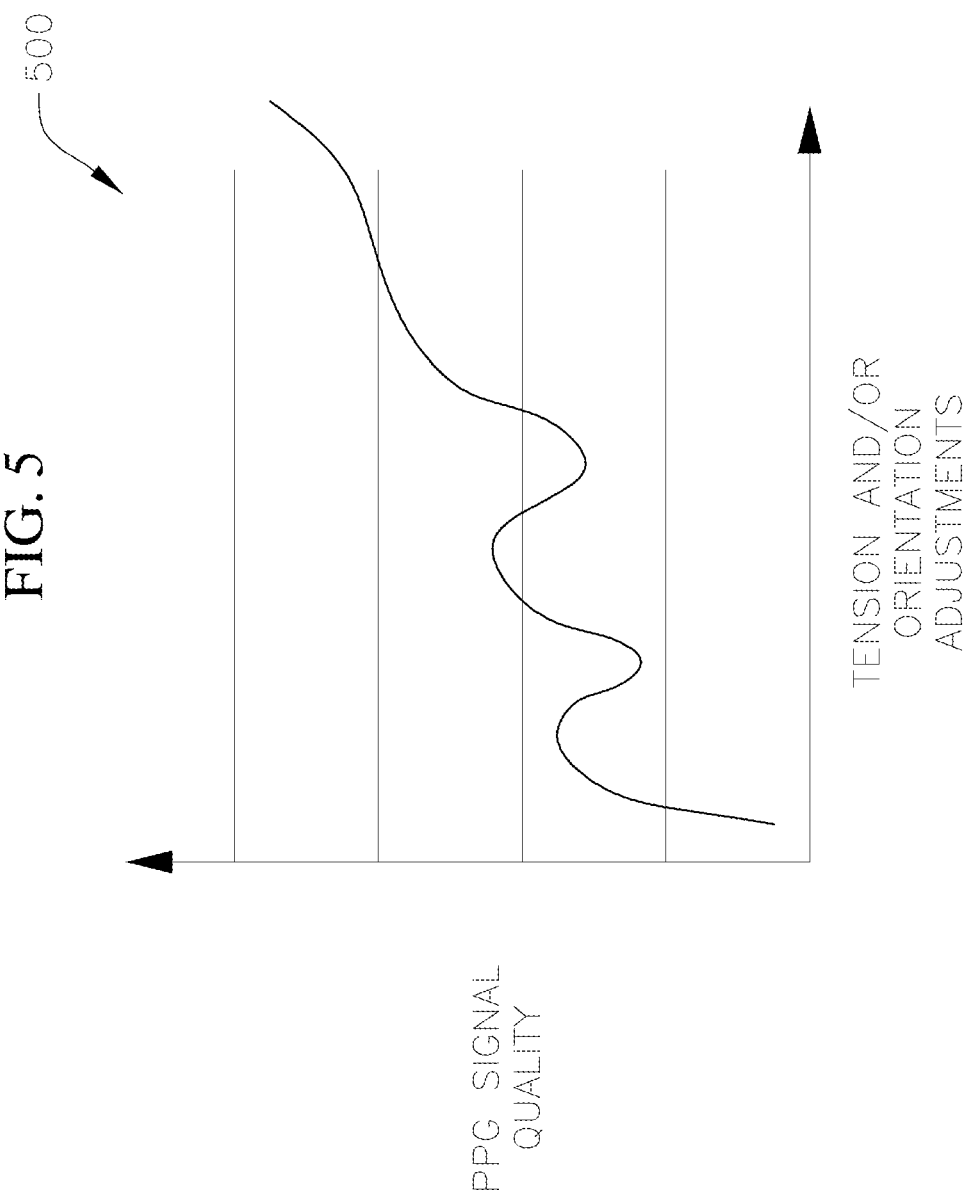

METHOD AND APPARATUS FOR OBTAINING HIGH QUALITY PHOTOPLETHYSMOGRAM DATA FROM WEARABLE

CROSS-REFERENCE TO RELATED APPLICATION(S)

This utility patent application claims priority to and the benefit of U.S. Provisional Patent Application Ser. No. 62/586,107, filed Nov. 14, 2017, titled "Method and Apparatus for Obtaining High Quality Photoplethysmogram Data from Wearable," the entire content of which is incorporated by reference herein.

BACKGROUND

A wearable device (e.g., a watch, a bracelet) may have mounted thereon one or more photoplethysmogram (PPG) sensors for monitoring and detecting vital signals (e.g., a heart rate) of a user wearing the wearable device. For example, a PPG sensor optically detects changes in the blood flow volume via optical reflection from or transmission through the user's tissue. A PPG sensor that is in close contact with a user's skin ensures that high quality measurements are obtained.

However, as the user may be moving in various situations, the wearable device may be moving (e.g., sliding up and down along the user's wrist), causing the PPG sensor to lose contact with the skin, thereby likely decreasing the accuracy of the measurements.

The above information disclosed in this Background section is only for enhancement of understanding of the background of the present disclosures, and therefore, it may contain information that does not form prior art.

SUMMARY

One or more example embodiments of the present disclosure are directed to a PPG sensor equipped band (i.e., a wristband or a wearable device including the band) that automatically adjusts a tension and/or an orientation of the band in real time to achieve a highest (or desired) PPG signal quality. The band according to example embodiments provides automated tension and/or orientation adjustments based on a quality of measured PPG signals.

According to example embodiments of the present disclosure, the wearable device includes one or more of a PPG sensor (or multiple PPG sensors), a motion sensor (e.g., inertial measurement unit (IMU), accelerometer, gyroscope, and/or the like), a tension sensor, and a flexible mechanical band (e.g., a wristband) that is controlled by one or more actuators (such as a motor (e.g., a small mechanical motor or micro-electro-mechanical)). The actuators may adjust the tension of the band and further rotate or tilt the band, thereby adjusting orientation of the band and the PPG sensor with respect to the wrist of the wearer of the wearable device.

The wearable device according to example embodiments of the present disclosure may further include a processor (or a processing unit) that uses a trained neural network to stir the system to gather a highest (or desired) quality PPG signal (or PPG signals). The adjusted tension and/or orientation of the band ensures that a desired (or optimum, maximum) contact with the user's skin is maintained to provide a desired PPG signal quality.

According to example embodiments, one or more neural networks may control or set the parameter (or parameters) of the band dynamically to get to desirable (or optimum) position and/or orientation for best signal quality (e.g., best PPG signal quality).

According to an example embodiment of the present disclosure, a wearable device includes: a wristband; at least one PPG sensor mounted on the wrist band and configured to output a measured PPG signal corresponding to vital signals of a wearer of the wristband; and a neural network based controller configured to receive the measured PPG signal from the at least one PPG sensor and to generate commands in real time based on a quality of the measured PPG signal to adjust at least one selected from a position, a tension, and an orientation of the wristband to achieve a desired PPG signal quality.

According to an example embodiment of the present disclosure, the wearable device may further include: an IMU sensor mounted on the wristband and configured to generate an IMU signal including at least one selected from position data, orientation data, and acceleration data; a tension sensor mounted on the wristband and configured to generate a tension signal; and an actuator mounted on the wristband and configured to adjust the at least one selected from the position, the tension, and the orientation of the wristband in response to one or more of the commands.

The adjusted at least one selected from the position, the tension, and the orientation may be suitable to maintain a desired contact with the wearer's skin to provide the desired PPG signal quality.

The neural network based controller may be configured to set one or more parameters of the wristband dynamically to adjust at least one selected from the position, the tension, and the orientation of the wristband to achieve the desired PPG signal quality.

The neural network based controller may be configured to receive a measured tension signal, and to output a tension adjustment command corresponding to the measured PPG signal and the measured tension signal from among the commands to control a tension experienced by the wristband.

The neural network based controller may include a first neural network based controller configured to receive the measured tension signal and a second neural network based controller configured to receive the measured PPG signal.

The second neural network based controller may be configured to compare the measured PPG signal against a referenced PPG signal to determine a probability of good signal quality, and the first neural network based controller may be configured to receive the probability of good PPG signal quality and to analyze the measured tension signal and the probability of good PPG signal quality against a trained model to generate the tension adjustment command.

The wearable device may further include a tension sensor to output the measured tension signal, and an orientation sensor to output a measured orientation signal, wherein the first neural network based controller may be further configured to receive the measured orientation signal, and to further analyze the measured orientation signal to generate an orientation adjustment command from among the commands.

The tension sensor may include a spring adapted to measure a force caused by stretching of the wristband.

The first neural network based controller may be configured to optimize a desired contact between the at least one PPG sensor and a wearer of the wearable device.

The second neural network based controller may include a quality assessment network trained using sample data having desired PPG signal quality and configured to analyze the measured PPG signal against the trained data based on reinforcement-learning to maximize a reward.

The wearable device may further include one or more actuators to adjust at least one selected from a tension of the wristband and an orientation of the at least one PPG sensor.

The sensor package may further include one or more gears adapted to engage a plurality of grooves at one end of the band to adjust the tension of the wristband according to operation of the one or more actuators.

According to an example embodiment of the present disclosure, a method of measuring vital signals utilizing a wearable device including a band, a processor comprising a first neural network based controller and a second neural network based controller, a plurality of PPG sensors, an actuator, a plurality of gears, a tension sensor and an orientation sensor, is provided. The method includes: measuring PPG signals utilizing the PPG sensors and providing the measured PPG signals to the second neural network based controller; measuring a tension signal utilizing the tension sensor and providing the measured tension signal to the first neural network based controller; measuring an orientation signal utilizing the orientation sensor and providing the measured orientation signal to the first neural network based controller; outputting a reward signal from the second neural network based controller and providing the reward signal to the first neural network based controller; and generating at least one selected from a tension adjustment command and an orientation adjustment command by the first neural network based controller to control the actuator to adjust at least one selected from the tension of the band and the orientation of the PPG sensors.

The actuator may be configured to control the gears to adjust the tension experienced by the band.

The band may include a plurality of grooves at one end, the plurality of grooves being adapted to engage the gears for adjusting the tension.

The actuator may be further configured to control the gears to adjust the orientation of the PPG sensors.

The first neural network based controller may be configured to receive a probability of good PPG signal quality and to analyze the probability of good PPG signal quality with the measured tension and orientation signals against a trained model to generate at least one selected from the tension adjustment command and the orientation adjustment command.

The second neural network based controller may be configured to compare the measured PPG signals against reference PPG signals to determine a probability of good PPG signal quality.

The second neural network based controller may include a quality assessment network trained using sample data having desired PPG signal quality and configured to analyze the measured PPG signals against the trained data based on reinforcement-learning to maximize a reward.

BRIEF DESCRIPTION OF THE DRAWINGS

The above and other aspects and features of the present disclosure will become apparent to those skilled in the art from the following detailed description of the example embodiments with reference to the accompanying drawings.

FIG. 1C is a schematic cross sectional view of the wearable device of FIG. 1A taken along the line 1C-1C of FIG. 1A.

FIG. 5 is an example of tension and/or orientation adjustments for various desired PPG signal quality, which the neural network will learn dynamically according to example embodiments of the present disclosure.

DETAILED DESCRIPTION

Figure 1A:
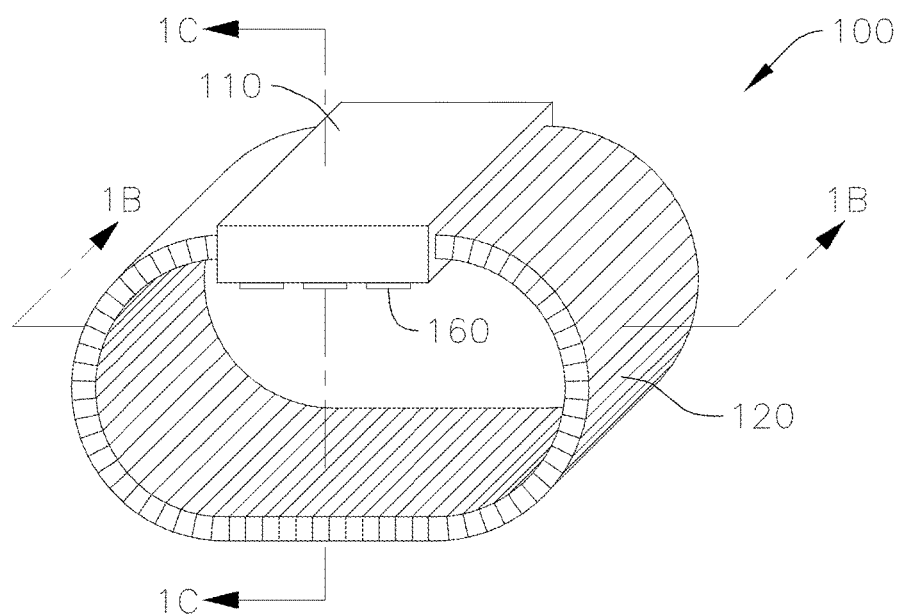
FIG. 1A is a perspective view of a band that shows its mechanical structure according to one embodiment of the present disclosure.

Hereinafter, example embodiments will be described in more detail with reference to the accompanying drawings, in which like reference numbers refer to like elements throughout. The present disclosure, however, may be embodied in various different forms, and should not be construed as being limited to only the illustrated embodiments herein. Rather, these embodiments are provided as examples so that this disclosure will be thorough and complete, and will fully convey the aspects and features of the present disclosure to those skilled in the art. Accordingly, processes, elements, and techniques that are not necessary to those having ordinary skill in the art for a complete understanding of the aspects and features of the present disclosure may not be described. Unless otherwise noted, like reference numerals denote like elements throughout the attached drawings and the written description, and thus, descriptions thereof will not be repeated. In the drawings, the relative sizes of elements, layers, and regions may be exaggerated for clarity.

It will be understood that, although the terms "first," "second," "third," etc., may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises," "comprising," "includes," and "including," when used in this specification, specify the presence of the stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of" and "at least one selected from," when preceding a list of elements, modify the entire list of elements and do not modify the individual elements of the list.

As used herein, the term "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present disclosure refers to "one or more embodiments of the present disclosure." As used herein, the terms "use," "using," and "used" may be considered synonymous with the terms "utilize," "utilizing," and "utilized," respectively.

The electronic or electric devices and/or any other relevant devices or components according to embodiments of the present disclosure described herein, such as a processor, neural networks, neural network based controllers, a motor, actuators, and various sensors may be implemented utilizing any suitable hardware, firmware (e.g. an application-specific integrated circuit), software, or a combination of software, firmware, and hardware. For example, the various components of these devices may be formed on one integrated circuit (IC) chip or on separate IC chips. Further, the various components of these devices may be implemented on a flexible printed circuit film, a tape carrier package (TCP), a printed circuit board (PCB), or formed on one substrate. Further, the various components of these devices may be a process or thread, running on one or more processors, in one or more computing devices, executing computer program instructions and interacting with other system components for performing the various functionalities described herein. The computer program instructions are stored in a memory which may be implemented in a computing device using a standard memory device, such as, for example, a random access memory (RAM). The computer program instructions may also be stored in other non-transitory computer readable media such as, for example, a CD-ROM, flash drive, or the like. Also, a person of skill in the art should recognize that the functionality of various computing devices may be combined or integrated into a single computing device, or the functionality of a particular computing device may be distributed across one or more other computing devices without departing from the spirit and scope of the exemplary embodiments of the present disclosure.

Unless otherwise defined, all terms (including technical and scientific terms) used herein have the same meaning as commonly understood by one of ordinary skill in the art to which the present disclosure belongs. It will be further understood that terms, such as those defined in commonly used dictionaries, should be interpreted as having a meaning that is consistent with their meaning in the context of the relevant art and/or the present specification, and should not be interpreted in an idealized or overly formal sense, unless expressly so defined herein.

Photoplethysmogram (PPG) sensors are used on wearable devices such as smart watches and sport wristbands to measure vital signals (e.g., a heart rate) of subjects. The primary caveats (or considerations) of such sensors are positional and motion sensitivity. For example, if the wristband is worn loosely or it is worn on the wrong spot on a wrist, the motion or location can corrupt the PPG sensor output (e.g., signals or output signals), thereby resulting in inaccurate heart rate estimates. Inaccurate heart rate estimates may result in customer dissatisfaction among other problems. To be able to perform medical diagnostics using PPG, the PPG-equipped band should be of highest quality possible. According to one or more example embodiments of the present disclosure, the PPG sensor data (e.g., output or output signal), the IMU sensor data (e.g., output or output signal), and tension sensor data (e.g., output or output signal) are input to a control algorithm that adjusts the tension and orientation of the band in a way to achieve high quality (e.g., desired or suitable quality) PPG signal continuously.

FIG. 1A is a perspective view of a wearable device 100 that shows its mechanical structure according to one example embodiment of the present disclosure. The wearable device 100 includes a band 120 and a sensor package 110. The sensor package (e.g., a main closure or a sensor/controller package) 110 is attached to the band and includes one or more gears to adjust the tension of the band 120. One or more actuators (e.g., a motor 150 of FIG. 1B) engage the one or more gears (e.g., gears 170 of FIG. 1B) to adjust the tension, tilt and/or orientation of the band 120, and therefore the sensor package 110, which holds one or more sensors (e.g., sensors 140, 160), actuators (e.g., the motor 150), gears (e.g., gears 170) and a processor (or a processing unit, e.g., a processor 130) illustrated in FIG. 1B.

The sensor package 110 includes and has mounted thereon one or more PPG sensors 160. By adjusting the tension of the band (120) and/or the orientation of the sensor package 110 (and therefore the PPG sensors 160) with respect to the wrist (e.g., the skin on the wrist) of the wearer of the wearable device, a high quality (e.g., a desired or suitable quality) PPG signals may be realized.

Figure 1B:
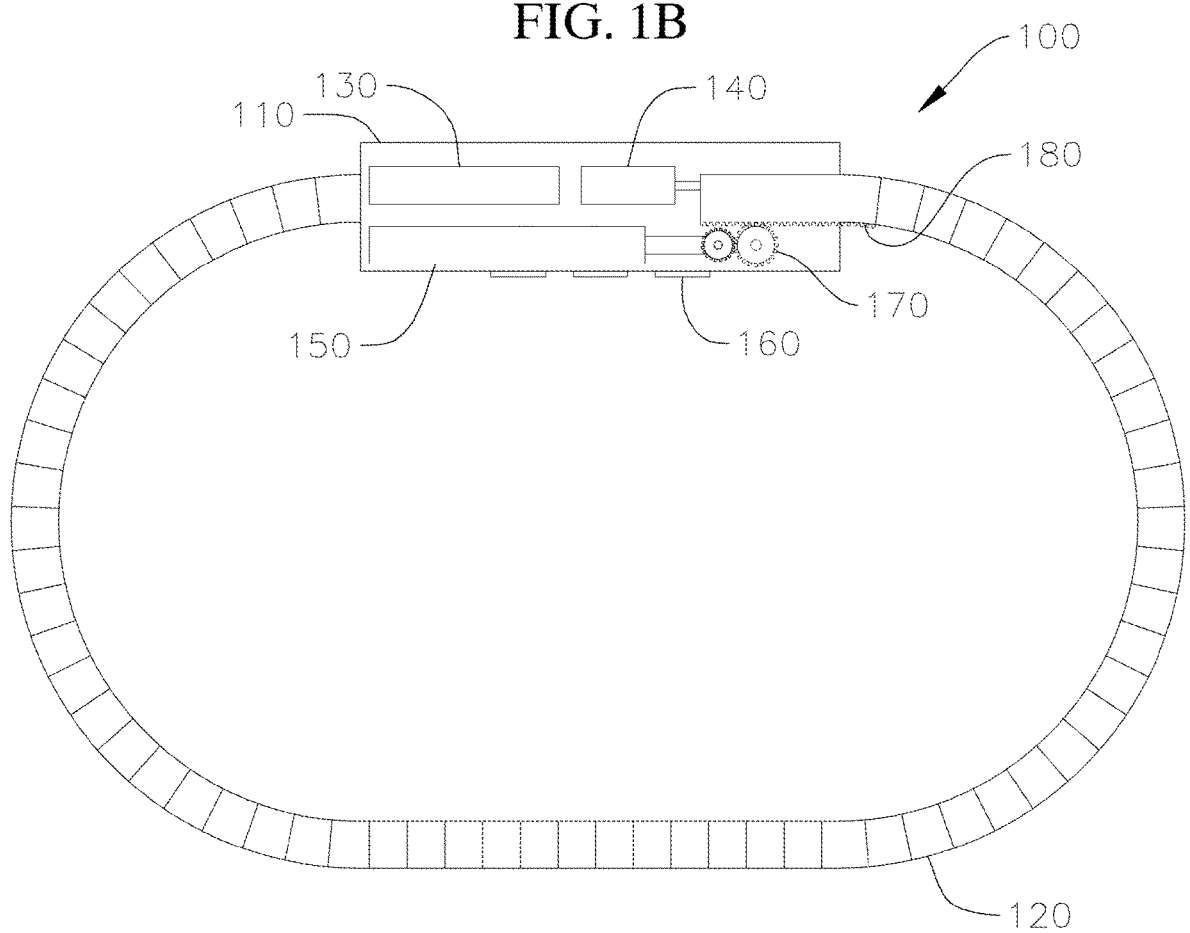
FIG. 1B is a schematic cross sectional view of the wearable device of FIG. 1A taken along the line 1B-1B of FIG. 1A.

FIG. 1B is a schematic cross sectional view of the wearable device 100 taken along the line 1B-1B of FIG. 1A. As can be seen in FIG. 1B, the sensor package 110 includes therein the processor 130, a tension sensor 140, the motor 150, the PPG sensors 160 and one or more gears 170. While it is not specifically illustrated in FIG. 1B, the sensor package 110 according to example embodiments may also include one or more other sensors (e.g., an IMU) to measure such characteristics as orientation, position, and acceleration data corresponding to the wearable device (and the PPG sensors), and one or more neural networks in the processor 130 to utilize such sensor data to generate commands to operate one or more actuators (e.g., the motor 150) to improve or optimize quality of the PPG signals.

According to example embodiments, the processor 130 uses a neural network reinforcement-learning method and operates based on good quality (or desired) PPG signal as the reward. For example, the network moves the actuators such that an amount or quantity by which the tension and/or orientation of the band 120 is adjusted from the current tension and/or orientation would improve or optimize the PPG signal quality. The neural network in the processor 130 is trained using simulated episodes of PPG signal (or PPG signals) generated from a physical model of the wearable device 100. An example goal of the neural network is to achieve best (or optimum) PPG signal quality by adjusting the tension and orientation of the band 120.

The tension sensor 140 is connected to the band 120 to detect the tension experienced by the band 120 and provide the detected tension information to the processor 130. Similarly, the PPG sensors 160 detect PPG information (e.g., corresponding to vital signals such as the heart rate) and provide PPG signals to the processor 130. The processor 130 controls the motor 150 (and/or one or more other actuators) to control the tension experienced by the band 120 as well as the tilt and/or orientation of the band 120 to adjust the orientation of the sensor package 110 (therefore, the PPG sensors 160) with respect to a wrist of the person wearing the wearable device 100, thereby adjusting both the tension and the orientation of the wearable device to optimize or improve detection of vital signals, such as the heart rate.

For example, to control the tension experienced by the band 120, the motor 150 is coupled to the band 120 via one or more gears 170 to either tighten or loosen the band 120 around the user's wrist. To that end, the band 120 has at one end a plurality of grooves 180 configured to engage the one or more gears 170 such that the end of the band 120 is moved toward or away from the other end of the band 120 depending on the direction of movement or rotation of a rotor in the motor 150.

To adjust the orientation of the wearable device with respect to the wrist (and therefore the skin on the wrist) of the user, the sensor package 110 according to example embodiments of the present disclosure also includes one or more other sensors such as an IMU, a gyroscope, a position sensor, an accelerometer, and/or the like, to measure a position, an angle, an orientation and/other measurements of the wearable device 100 with respect to the wrist of the person, and/or the acceleration being experienced by the wearable device. These other sensors and their functions will be described in more detail in reference to FIGS. 2 and 3.

FIG. 1C is a schematic cross sectional view of the wearable device 100 of FIG. 1A taken along the line 1C-1C of FIG. 1A. As shown in FIG. 1C, the sensor package 110 also includes one or more actuators (and/or gears) 190 for adjusting an orientation of and/or rotating the band 120 with respect to the wrist of a user. The one or more actuators 190 may include a rotation actuator, for example.

Figure 2:
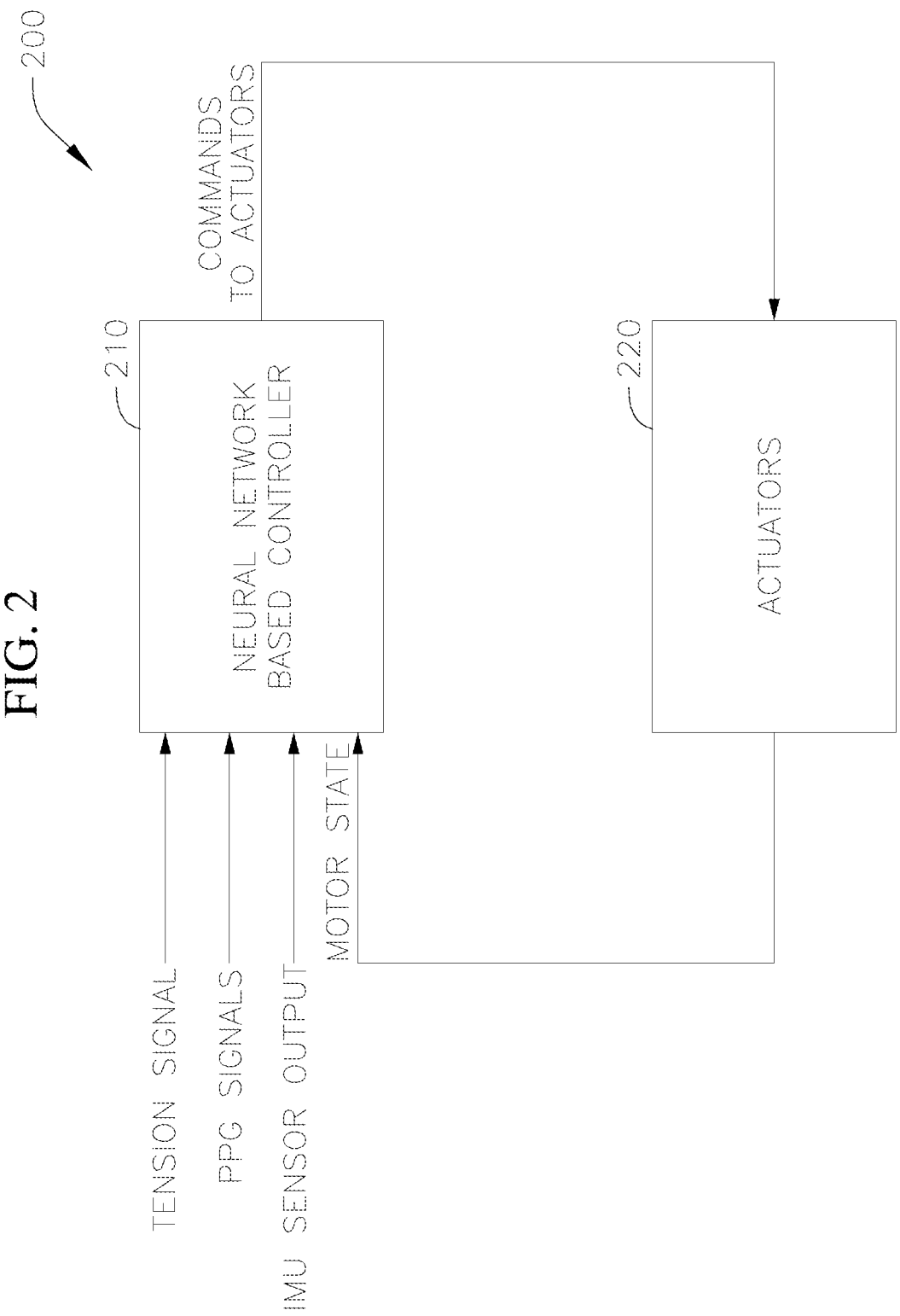
FIG. 2 is a control diagram for actuators using a neural network based controller in a wearable device according to example embodiments of the present disclosure.

FIG. 2 is a control diagram of actuators 220 using a neural network based controller 210 in a wearable device 200 according to example embodiments of the present disclosure. The wearable device 200 may be the same or substantially similar to the wearable device 100 of FIGS. 1A-1C. For example, the actuators 220 may correspond to the motor 150 of FIG. 1B, and the neural network based controller 210 may be implemented in the processor 130 of FIG. 1B.

The neural network based controller 210 receives one or more sensor signals, which may include but are not limited to, a tension signal, one or more PPG signals, and an inertial measurement unit (IMU) sensor output (e.g., position, acceleration, angle, and/or orientation signals), and outputs one or more commands (e.g., motor commands) to the actuators 220. The motor commands may include, but are not limited to, a tension control command and an orientation control command. The motor may also provide a motor state signal as a feedback to the neural network based controller 210.

In example embodiments, the actuators 220 may include one or more motors and/or one or more actuators for adjusting the tension and/or orientation of the band (e.g., the band 120 of FIGS. 1A-1B). Further, the measured tension signal may be a measured tension signal provided by a tension sensor (e.g., the tension sensor 140 of FIGS. 1A-1B), and the IMU sensor output signal may be provided by an orientation sensor mounted in the sensor package 110 of FIGS. 1A-1B. As used herein, the term "orientation sensor" may refer to one or more of various sensors for measuring position, orientation (e.g., angle) and/or acceleration experienced by the wearable device 200, and may include, but are not limited to an IMU, a position sensor, an accelerometer and/or a gyroscope used to measure and output signals used to adjust the orientation of the wearable device 200 (or the wearable device 100), and therefore the band and the PPG sensors, with respect to the wrist of the person wearing the wearable device.

Figure 3:
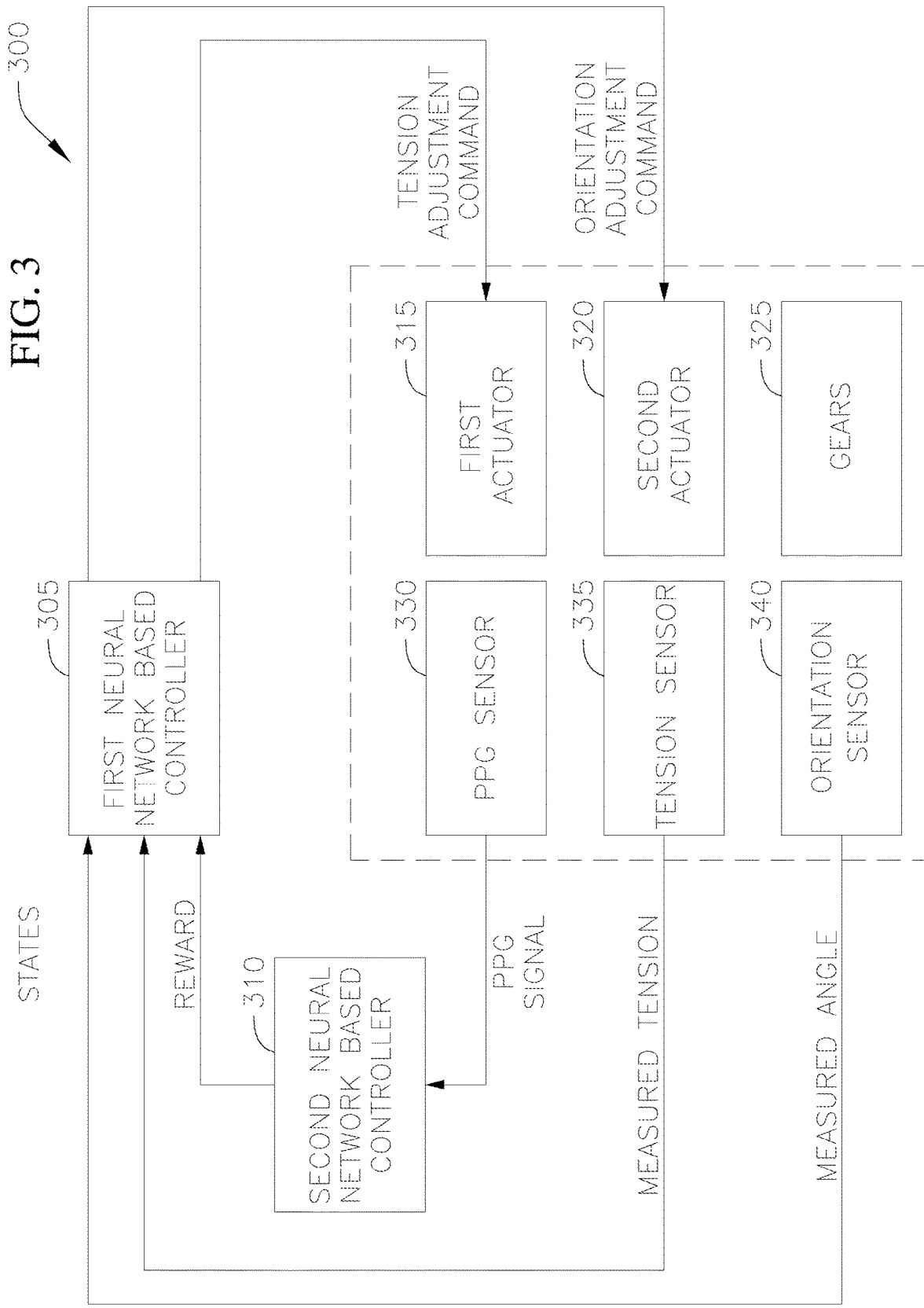
FIG. 3 is a system block diagram of a wearable device according to example embodiments of the present disclosure.

FIG. 3 is a system block diagram of a wearable device 300 according to example embodiments of the present disclosure. The wearable device 300 may automatically adjust tension and/or orientation of a band (or a wristband, for example, the band 100 of FIGS. 1A-1B) based on a quality of measured PPG signals. The wearable device 300, for example, may correspond to or be used as the wearable device 100 of FIGS. 1A-1B and/or the wearable device 200 of FIG. 2.

The wearable device 300 includes a first neural network based controller 305 and a second neural network based controller 310, but are not limited thereto, and may include one or more additional neural networks or neural network based controllers. The first and second neural network based controllers 305, 310 and/or one or more other neural network based controllers may together be referred to as a neural network based controller herein. Also, the term "a neural network based controller" may be used interchangeably with "a neural network based processor." Further, the neural network based controllers 305 and 310 may be integrated into a single neural network based controller in some embodiments. The first neural network based controller 305 may receive tension and/or orientation (e.g., angle) measurements and a probability of good PPG signal quality, and analyzes received data (e.g., the measurements and the probability of good PPG signal quality) against a trained model to determine desired tension and/or orientation adjustments to the band (e.g., the band 120 of FIGS. 1A-1B).

The second neural network based controller 310 may receive measured PPG signals and compare the measured PPG signals against trained PPG signals to determine a probability of good PPG signal quality, and provide the probability of good PPG signal quality to the first neural network based controller 305. For example, the probability of good PPG signal is a probability that an amount or quantity of adjustment for the tension and/or orientation of the band from the current tension and/or orientation would improve or optimize the PPG signal quality, and corresponds to the reward function of the second neural network based controller 310.

The wearable device 300 also includes a first actuator 315 and a second actuator 320, but are not limited thereto, and may include one or more other actuators and/or motors as those skilled in the art would appreciate. The first and second actuators 315 and 320, for example, may include the motor 150 of FIG. 1B or the actuators 220 of FIG. 2. According to example embodiments of the present disclosure, the actuators 315 and 320 receive tension and/or orientation adjustment signals (or commands), and adjust or control gears in the band (e.g., the band 120 of FIGS. 1A-1B) such that the band maintains a desirable (e.g., an improved or optimum) contact with the wrist of the user for realizing desired PPG signal quality of the measured PPG signals.

The wearable device 300 also includes one or more PPG sensors 330 (which may be similar to the PPG sensors 160 of FIGS. 1A-1B), a tension sensor 335 (which may be similar to the tension sensor 140 of FIG. 1B) and an orientation sensor 340. As used herein, the term "orientation sensor" may refer to one or more of various sensors for measuring position, orientation (e.g., angle) and/or acceleration experienced by the wearable device 300, and may include, but are not limited to an IMU, a position sensor, an accelerometer and/or a gyroscope used to measure and output signals used to adjust the orientation of the wearable device 300, and therefore the band and the PPG sensors, with respect to the wrist of the person wearing the wearable device.

According to example embodiments, the first neural network based controller 305 may be a type of controller (e.g., a proportional-integral-derivative (PID) controller) that receives inputs including states (tension measurements, orientation measurements, acceleration measurements, and/or the like) provided by the tension sensor 335 and the orientation sensor 340 in the wearable device 300. For example, the tension sensor 340 may be in the form of a spring that measures a force (Newton) caused by the stretched band (e.g., the wristband) 120 of the wearable device 100. The orientation sensor 340 may measure an angle of the PPG sensor (or PPG sensors) 330 relative to the user's wrist. The orientation sensor 340 may also measure the position of the PPG sensors with respect to the wrist and/or the acceleration experienced by the PPG sensors. In various embodiments, the first neural network based controller 305 may have any suitable neural network architecture known to those skilled in the art, and may have been trained using any suitable sample data known to those skilled in the art.

The second neural network based controller 310 receives measured PPG signals provided by the PPG sensor (or the PPG sensors) 330 in the wearable device 300. The second neural network based controller 310 may be trained using sample data having desired PPG signal quality and analyzes the measured PPG signals against the trained data based on reinforcement-learning (e.g., a Markov decision process) to maximize or improve a reward. By analyzing (or comparing) the measured PPG signals against trained PPG signals, the second neural network based controller 310 generates the reward that corresponds to the probability of good PPG signal quality, and provides the reward to the first neural network based controller 305.

The first neural network based controller 305 analyzes the tension and/or orientation measurements received from the sensors and the reward (e.g., corresponding to the probability of good PPG signal quality) received from the second neural network based controller 310 against a trained model to determine desired tension and/or orientation adjustments to the band (e.g., the band 120 of FIGS. 1A-1B), and provides tension and/or orientation adjustment commands to the first and second actuators 315 and 320. In other words, the first neural network based controller 305 analyzes the received states (e.g., the tension and/or orientation measurements) and rewards against a trained model (e.g., as shown in FIG. 5) of desired tension and/or orientation adjustments for various desired PPG signal qualities.

The first actuator 315 receives the tension adjustment command from the first neural network based controller 305 to adjust the tension of the band (e.g., the band 120 of FIGS. 1A-1B) by engaging and controlling (or adjusting) one or more of the gears 325. The gears 325 may correspond to the gears 170 of FIG. 1B and/or the gears 190 of FIG. 1C, for example. The second actuator 320 receives the orientation adjustment command from the first neural network based controller 305 to adjust the orientation of the PPG sensors 330 (e.g., the sensor package 110 of FIGS. 1A-1B on which the PPG sensors 160 are mounted) to optimize or improve the PPG signal output from the one or more PPG sensors 330. To calculate the amount of adjustments to be performed in response to the tension and orientation adjustment commands, the first neural network based controller 305 receives the measured tension signal from the tensions sensor 335 and the measured angle signal (or the measured orientation signal) from the orientation sensor 340, respectively. The first neural network based controller 305 outputs the desired tension and/or orientation adjustment commands to respective actuators 315, 320 that tune the gears within the wristband of the wearable device 300 and improves or optimizes the wearable device 300 so that the PPG sensors 330 maintain a desired contact with the wrist of the user. A combination of the desired tension and orientation adjustments may be tuned to improve or optimize the desired contact between the PPG sensors and the wrist of the user.

Figure 4:
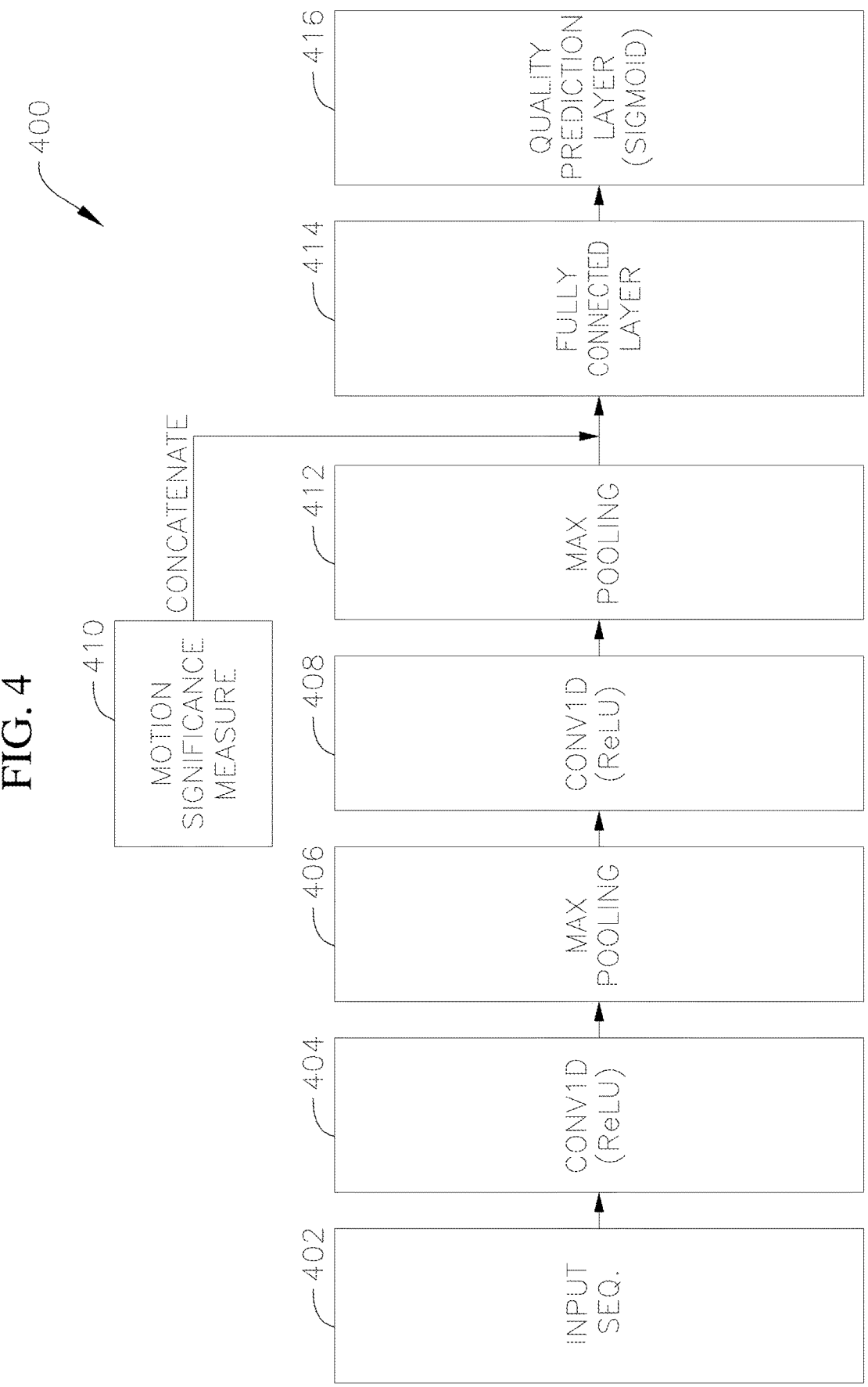
FIG. 4 is an example diagram of the neural network 2 of FIG. 3 that may be in the form of a quality assessment network, according to one or more embodiments of the present disclosure.

FIG. 4 is an example diagram of the second neural network based controller 310 of FIG. 3 that may be in the form of a quality assessment network (or quality assessment network architecture) 400, according to one or more example embodiments of the present disclosure. According to example embodiments, the structure of the 1D convolutional layers in FIG. 4 may be noted as N×D where N is the number of filters and D is the length of each filter. While the layers of the second neural network based controller 310 are illustrated in FIG. 4 by way of example, in various embodiments, the second neural network based controller 310 may have any suitable neural network architecture known to those skilled in the art, and may have been trained using any suitable sample data known to those skilled in the art.

The quality assessment network 400 may be a multimodal neural network that is designed to accept two inputs, the preprocessed PPG signal with length of 30 seconds and a vigorous motion measure, and predicts the probability of a signal being good quality or not. By way of example, the vigorous motion may be calculated by thresholding the percentage of standard deviations on half-second window over 30-second Accelerometer data segment. The motion variable is injected at the last stage along with learned features of PPG. The model may be trained by the quality label constructed as targets.

According to example embodiments, for an input layer 402 of the quality assessment network 400, the input sequence size may be 3,000. The quality assessment network 400 includes two pairs of a convolutional layer 404, 408 and a max pooling layer 406, 412, followed by two layers of fully connected layer (i.e., a fully connected layer 414 and a quality prediction layer 416). The first convolutional layer 404 may have 4 filters of size 4×1. The first pooling layer 406 may have a maximum pooling size of 12. The second convolutional layer 408 may have 4 filters with size 2×4. The second pooling layer 412 may have a maximum pooling size of 8. The output from the convolutional layers 404, 408 are flattened and concatenated with the motion significance measure 410 for that signal and is fed into two fully connected layers (i.e., the fully connected layer 414 and the quality prediction layer 416). By way of example, the output size of the fully connected layer 414 may be 64 according to some example embodiments.

According to example embodiments, Rectified Linear Units (ReLU) are used in the convolutional layers 404, 408 for activation function, except for the last fully connected layer 416, which has a Sigmoid activation function to output the probability (e.g., a probability of good PPG signal quality). The weights of the model may be improved or optimized by Adam Algorithm, using binary cross-entropy as loss function, for example.

The model according to example embodiments of the present disclosure is regularized to prevent overfitting. With L2 regularization imposed on the weights of two convolutional layers 404, 408 and a drop-out layer (e.g., a drop-out layer in or adjacent to the fully connected layer 414) between two fully connected layers. The parameter for L2 regularization may be 0.05 and rate for drop-out layer may be set to 0.5 or 0.7. According to an example embodiment, the model may be evaluated with 5 fold cross-validation, and the performance metric may be calculated as the mean of the accuracy of the test set in each fold, as well as a pooled AUC across all folds. Total number of parameter of this model according to example embodiments of the present disclosure may be 8,249 and 99.3% of parameters may be from fully connected layers.

Although the present disclosure has been described with reference to the example embodiments, those skilled in the art will recognize that various changes and modifications to the described embodiments may be performed, all without departing from the spirit and scope of the present disclosure. Furthermore, those skilled in the various arts will recognize that the present disclosure described herein will suggest solutions to other tasks and adaptations for other applications. It is the applicant's intention to cover by the claims herein, all such uses of the present disclosure, and those changes and modifications which could be made to the example embodiments of the present disclosure herein chosen for the purpose of disclosure, all without departing from the spirit and scope of the present disclosure. Thus, the example embodiments of the present disclosure should be considered in all respects as illustrative and not restrictive, with the spirit and scope of the present disclosure being indicated by the appended claims, and their equivalents. Further, those skilled in the art would appreciate that one or more features according to one more embodiments of the present disclosure may be combined with one or more other features according to one or more other embodiments of the present disclosure without departing from the spirit and scope of the present disclosure.

What is claimed is:

1. A wearable device comprising:
   a wristband;
   at least one photoplethysmogram (PPG) sensor mounted on the wristband and configured to output a measured PPG signal corresponding to vital signals of a wearer of the wristband;
   a tension sensor mounted on the wristband and configured to output a measured tension signal;
   a neural network based controller configured to receive the measured tension signal and the measured signal from the at least one PPG sensor, and generate commands in real time based on results of a determination made for the measured PPG signal to adjust a tension of the wristband to achieve a desired PPG signal quality; and
   one or more actuators to adjust the at least one selected from the position, tension, and orientation of the wristband, in response to the commands,
   wherein the neural network based controller is further configured to analyze input data including the measured tension signal and the results of the determination made for the measured PPG signal, and output a tension adjustment command predicted to achieve the desired PPG signal quality, wherein the analyzing includes comparing the input data against a trained neural network model.

2. The wearable device of claim 1, further comprising:
   an inertial measurement unit (IMU) sensor mounted on the wristband and configured to generate an IMU signal comprising at least one selected from position data, orientation data, and acceleration data.

3. The wearable device of claim 1, wherein the neural network based controller is configured to set commands for the actuators to maintain a desired contact with a wearer's skin to provide the desired PPG signal quality.

4. The wearable device of claim 1, wherein the neural network based controller comprises a first neural network based controller configured to receive the measured tension signal and a second neural network based controller configured to receive the measured PPG signal.

5. The wearable device of claim 4, wherein the second neural network based controller is configured to compare the measured PPG signal against a trained PPG signal to determine a probability of good signal quality, and the first neural network based controller is configured to receive the probability of good signal quality and to analyze the measured tension signal and the probability of good signal quality against the trained neural network model to generate the tension adjustment command.

6. The wearable device of claim 5, further comprising an orientation sensor to output a measured orientation signal, wherein the first neural network based controller is further configured to receive the measured orientation signal, and to further analyze the measured orientation signal to generate an orientation adjustment command from among the commands.

7. The wearable device of claim 4, wherein the first neural network based controller is configured to optimize a desired contact between the at least one PPG sensor and a wearer of the wearable device.

8. The wearable device of claim 4, wherein the second neural network based controller comprises a quality assessment network trained using sample data having desired PPG signal quality and configured to analyze the measured PPG signal against the trained data based on reinforcement-learning to maximize a reward.

9. The wearable device of claim 1, wherein the tension sensor comprises a spring adapted to measure a force caused by stretching of the wristband.

10. The wearable device of claim 1 further comprising one or more gears adapted to engage a plurality of grooves at one end of the wristband to adjust the tension of the wristband according to operation of the one or more actuators.

11. The wearable device of claim 1, wherein the neural network based controller is further configured to compare the measured PPG signal against trained PPG signals to determine a probability that the measured PPG signal satisfies a criterion, and return results of the comparing as the results of the determination made for the measured PPG signal.

12. A method of measuring vital signals utilizing a wearable device comprising a band, a processor comprising a first neural network based controller and a second neural network based controller, a plurality of photoplethysmogram (PPG) sensors, an actuator, a plurality of gears, a tension sensor, the method comprising:
   measuring PPG signals utilizing the PPG sensors and providing the measured PPG signals to the second neural network based controller;
   measuring a tension signal utilizing the tension sensor and providing the measured tension signal to the first neural network based controller;
   outputting, by the second neural network based controller, results of a determination made for the measured PPG signals, and providing the results to the first neural network based controller;
   analyzing, by the first neural network based controller, input data including the measured tension signal and the results of the determination made for the measured PPG signals, and outputting a tension adjustment command predicted to achieve a desired PPG signal quality, wherein the analyzing includes comparing the input data against a trained neural network model; and generating a tension adjustment command by the first neural network based controller to control the actuator to adjust tension of the band.

13. The method of claim 12, further comprising controlling, by the actuator, the gears to adjust the tension experienced by the band.

14. The method of claim 13 further comprising engaging the gears via grooves of the band for adjusting the tension.

15. The method of claim 14 further comprising controlling the gears to adjust orientation of the PPG sensors.

16. The method of claim 15 further comprising receiving, by the first neural network based controller, a probability of good PPG signal quality and analyzing the probability of good PPG signal quality with the measured tension signal against the trained neural network model to generate the tension adjustment command.

17. The method of claim 12, further comprising comparing, by the second neural network based controller, the measured PPG signals against trained PPG signals to determine a probability of good PPG signal quality, and returning results of the comparing as the results of the determination made for the measured PPG signals.

18. The method of claim 12, wherein the second neural network based controller comprises a quality assessment network trained using sample data having desired PPG signal quality, wherein the method further includes analyzing, by the quality assessment network, the measured PPG signals against trained data based on reinforcement-learning to maximize a reward.

\* \* \* \* \*